United States Patent
Smith et al.

(10) Patent No.: US 9,101,359 B2
(45) Date of Patent: Aug. 11, 2015

(54) SURGICAL STAPLE CARTRIDGE WITH SELF-DISPENSING STAPLE BUTTRESS

(75) Inventors: Bret W. Smith, Kings Mills, OH (US); Thomas W. Lytle, IV, Liberty Township, OH (US); Matthew C. Miller, Cincinnati, OH (US); Yi-Lan Wang, Belle Mead, NJ (US); Joseph Zavatsky, Flemington, NJ (US); Kreena Modi, Akron, OH (US); Aron O. Zingman, Cambridge, MA (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 875 days.

(21) Appl. No.: 13/231,064

(22) Filed: Sep. 13, 2011

(65) Prior Publication Data

US 2013/0062394 A1    Mar. 14, 2013

(51) Int. Cl.
*A61B 17/068* (2006.01)
*A61B 17/072* (2006.01)

(52) U.S. Cl.
CPC . *A61B 17/07292* (2013.01); *A61B 2017/07214* (2013.01); *A61B 2017/07271* (2013.01)

(58) Field of Classification Search
CPC .................. A61B 17/068; A61B 17/07292
USPC .......... 227/175.1, 176.1, 180.1; 606/139, 151
See application file for complete search history.

(56) References Cited

U.S. PATENT DOCUMENTS

| | | |
|---|---|---|
| 2,303,131 A | 11/1942 | Morgan |
| 3,364,200 A | 1/1968 | Ashton et al. |
| 3,496,940 A | 2/1970 | Steinman |
| 3,526,228 A | 9/1970 | Lyng |
| 4,222,383 A | 9/1980 | Schossow |
| 4,513,746 A | 4/1985 | Aranyi et al. |
| 4,549,545 A | 10/1985 | Levy |
| 4,610,250 A | 9/1986 | Green |
| 4,693,720 A | 9/1987 | Scharnberg et al. |

(Continued)

FOREIGN PATENT DOCUMENTS

| | | |
|---|---|---|
| CA | 481943 | 2/1947 |
| EP | 328 401 | 8/1989 |

(Continued)

OTHER PUBLICATIONS

International Search Report dated Dec. 10, 2012 for Application No. PCT/US2012/054388.

(Continued)

*Primary Examiner* — Michelle Lopez
(74) *Attorney, Agent, or Firm* — Frost Brown Todd LLC

(57) ABSTRACT

A surgical instrument includes a handle portion, a shaft housing a firing bar, an end effector comprising an anvil, a lower jaw, and a stapling and severing assembly responsive to a longitudinal closing motion produced by the handle portion and the shaft. The lower jaw is configured to receive a removable cartridge when in an open position. The cartridge includes a housing, a plurality of staples disposed in the housing, and a deck disposed over the plurality of staples. The deck defines apertures, with each aperture being substantially disposed over each staple. The instrument includes a movable buttress that is integral with the housing of the cartridge or integral with the lower jaw of the end effector. The buttress may attach to the anvil and include a portion to receive tissue. The receipt of tissue urges and moves the buttress proximally inwards to further encompass the tissue.

15 Claims, 11 Drawing Sheets

(56) References Cited

U.S. PATENT DOCUMENTS

| | | | |
|---|---|---|---|
| 4,805,823 A | 2/1989 | Rothfuss | |
| 5,011,493 A | 4/1991 | Belykh et al. | |
| 5,064,057 A | 11/1991 | Iwatsuki et al. | |
| 5,263,629 A | 11/1993 | Trumbull et al. | |
| 5,282,829 A | 2/1994 | Hermes | |
| 5,297,324 A | 3/1994 | Su | |
| 5,327,914 A | 7/1994 | Shlain | |
| 5,366,480 A | 11/1994 | Corriveau et al. | |
| 5,383,904 A | 1/1995 | Totakura et al. | |
| 5,393,594 A | 2/1995 | Koyfman et al. | |
| 5,411,193 A | 5/1995 | Culp | |
| 5,415,334 A | 5/1995 | Williamson, IV et al. | |
| 5,465,895 A | 11/1995 | Knodel et al. | |
| 5,466,462 A | 11/1995 | Rosenthal et al. | |
| 5,496,603 A | 3/1996 | Riedel et al. | |
| 5,503,638 A | 4/1996 | Cooper et al. | |
| 5,542,594 A | 8/1996 | McKean et al. | |
| 5,565,210 A | 10/1996 | Rosenthal et al. | |
| 5,597,107 A | 1/1997 | Knodel et al. | |
| 5,607,590 A | 3/1997 | Simizu | |
| 5,607,686 A | 3/1997 | Totakura et al. | |
| 5,632,432 A | 5/1997 | Schulze et al. | |
| 5,639,851 A | 6/1997 | Bezwada et al. | |
| 5,641,566 A | 6/1997 | Kranzler et al. | |
| 5,644,002 A | 7/1997 | Cooper et al. | |
| 5,673,840 A | 10/1997 | Schulze et al. | |
| 5,690,675 A | 11/1997 | Sawyer et al. | |
| 5,704,534 A | 1/1998 | Huitema et al. | |
| 5,711,958 A | 1/1998 | Cohn et al. | |
| 5,733,308 A | 3/1998 | Daugherty et al. | |
| 5,749,968 A | 5/1998 | Melanson et al. | |
| 5,752,965 A | 5/1998 | Francis et al. | |
| 5,755,778 A | 5/1998 | Kleshinski | |
| 5,766,188 A | 6/1998 | Igaki | |
| 5,769,892 A | 6/1998 | Kingwell | |
| 5,810,855 A | 9/1998 | Rayburn et al. | |
| 5,814,055 A | 9/1998 | Knodel et al. | |
| 5,814,057 A | 9/1998 | Oi et al. | |
| 5,833,695 A * | 11/1998 | Yoon | 606/139 |
| 5,843,096 A | 12/1998 | Igaki et al. | |
| 5,902,312 A | 5/1999 | Frater et al. | |
| 5,997,895 A | 12/1999 | Narotam et al. | |
| 6,019,791 A | 2/2000 | Wood | |
| 6,031,148 A | 2/2000 | Hayes et al. | |
| 6,099,551 A | 8/2000 | Gabbay | |
| 6,174,333 B1 | 1/2001 | Kadiyala et al. | |
| 6,203,564 B1 | 3/2001 | Hutton et al. | |
| 6,245,081 B1 | 6/2001 | Bowman et al. | |
| 6,273,897 B1 | 8/2001 | Dalessandro et al. | |
| 6,277,397 B1 | 8/2001 | Shimizu | |
| 6,312,474 B1 | 11/2001 | Francis et al. | |
| 6,325,810 B1 | 12/2001 | Hamilton et al. | |
| 6,355,699 B1 | 3/2002 | Vyakarnam et al. | |
| 6,488,197 B1 | 12/2002 | Whitman | |
| 6,495,127 B1 | 12/2002 | Wallace et al. | |
| 6,511,748 B1 | 1/2003 | Barrows | |
| 6,592,597 B2 | 7/2003 | Grant et al. | |
| 6,638,285 B2 | 10/2003 | Gabbay | |
| 6,656,193 B2 | 12/2003 | Grant et al. | |
| 6,704,210 B1 | 3/2004 | Myers | |
| 6,814,741 B2 | 11/2004 | Bowman et al. | |
| 6,835,336 B2 | 12/2004 | Watt | |
| 6,921,412 B1 | 7/2005 | Black et al. | |
| 6,962,594 B1 | 11/2005 | Thevenet | |
| 6,964,363 B2 | 11/2005 | Wales et al. | |
| 6,978,921 B2 | 12/2005 | Shelton, IV et al. | |
| 6,988,649 B2 | 1/2006 | Shelton, IV et al. | |
| 7,000,818 B2 | 2/2006 | Shelton, IV et al. | |
| 7,048,755 B2 | 5/2006 | Bonutti et al. | |
| 7,084,082 B1 | 8/2006 | Shimizu | |
| 7,111,769 B2 | 9/2006 | Wales et al. | |
| 7,143,923 B2 | 12/2006 | Shelton, IV et al. | |
| 7,147,138 B2 | 12/2006 | Shelton, IV | |
| 7,207,471 B2 | 4/2007 | Heinrich et al. | |
| 7,211,093 B2 | 5/2007 | Sauer et al. | |
| 7,268,205 B2 | 9/2007 | Williams et al. | |
| 7,303,108 B2 | 12/2007 | Shelton, IV | |
| 7,335,212 B2 | 2/2008 | Edoga et al. | |
| 7,367,485 B2 | 5/2008 | Shelton, IV et al. | |
| 7,377,928 B2 | 5/2008 | Zubik et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,455,208 B2 | 11/2008 | Wales et al. | |
| 7,517,356 B2 | 4/2009 | Heinrich | |
| 7,607,557 B2 | 10/2009 | Shelton, IV et al. | |
| 7,665,646 B2 * | 2/2010 | Prommersberger | 227/175.1 |
| 7,708,180 B2 | 5/2010 | Murray et al. | |
| 7,721,930 B2 | 5/2010 | McKenna et al. | |
| 7,738,971 B2 | 6/2010 | Swayze et al. | |
| 7,845,533 B2 | 12/2010 | Marczyk et al. | |
| 2002/0165559 A1 | 11/2002 | Grant et al. | |
| 2003/0120284 A1 | 6/2003 | Palacios et al. | |
| 2003/0183671 A1 | 10/2003 | Mooradian et al. | |
| 2004/0093024 A1 | 5/2004 | Lousararian et al. | |
| 2004/0167572 A1 | 8/2004 | Roth et al. | |
| 2004/0254608 A1 | 12/2004 | Huitema et al. | |
| 2005/0042250 A1 | 2/2005 | Damien et al. | |
| 2005/0059996 A1 | 3/2005 | Bauman et al. | |
| 2005/0070929 A1 | 3/2005 | Dalessandro et al. | |
| 2005/0101834 A1 | 5/2005 | Merade | |
| 2005/0107810 A1 | 5/2005 | Morales et al. | |
| 2005/0145671 A1 | 7/2005 | Viola | |
| 2005/0154403 A1 | 7/2005 | Sauer et al. | |
| 2005/0245965 A1 | 11/2005 | Orban III et al. | |
| 2005/0249772 A1 | 11/2005 | Malaviya et al. | |
| 2005/0251153 A1 | 11/2005 | Sakamoto et al. | |
| 2005/0283256 A1 | 12/2005 | Sommerich et al. | |
| 2005/0288767 A1 | 12/2005 | Kujawski et al. | |
| 2006/0004388 A1 | 1/2006 | Whayne et al. | |
| 2006/0047312 A1 | 3/2006 | Olmo et al. | |
| 2006/0093655 A1 | 5/2006 | Bar et al. | |
| 2006/0094318 A1 | 5/2006 | Matsuda et al. | |
| 2006/0135992 A1 | 6/2006 | Bettuchi et al. | |
| 2006/0173470 A1 | 8/2006 | Oray et al. | |
| 2006/0212069 A1 | 9/2006 | Shelton, IV | |
| 2006/0229672 A1 | 10/2006 | Forsberg | |
| 2006/0265006 A1 | 11/2006 | White et al. | |
| 2006/0265007 A1 | 11/2006 | White et al. | |
| 2007/0016227 A1 | 1/2007 | de la Torre et al. | |
| 2007/0034667 A1 | 2/2007 | Holsten et al. | |
| 2007/0034669 A1 | 2/2007 | de la Torre et al. | |
| 2007/0049953 A2 | 3/2007 | Shimoji et al. | |
| 2007/0060932 A1 | 3/2007 | Stack et al. | |
| 2007/0066981 A1 | 3/2007 | Meagher | |
| 2007/0112360 A1 | 5/2007 | De Deyne et al. | |
| 2007/0128243 A1 | 6/2007 | Serafica et al. | |
| 2007/0131732 A1 | 6/2007 | Holsten et al. | |
| 2007/0150002 A1 | 6/2007 | Szabo et al. | |
| 2007/0156140 A1 | 7/2007 | Baily | |
| 2007/0190108 A1 | 8/2007 | Datta et al. | |
| 2007/0207180 A1 | 9/2007 | Tanihara et al. | |
| 2007/0213522 A1 | 9/2007 | Harris et al. | |
| 2007/0219571 A1 | 9/2007 | Balbierz et al. | |
| 2007/0225642 A1 | 9/2007 | Houser et al. | |
| 2007/0243227 A1 | 10/2007 | Gertner | |
| 2007/0246505 A1 | 10/2007 | Pace-Floridia et al. | |
| 2007/0286892 A1 | 12/2007 | Herzberg et al. | |
| 2008/0039871 A1 | 2/2008 | Wallace et al. | |
| 2008/0077131 A1 | 3/2008 | Yates et al. | |
| 2008/0078800 A1 | 4/2008 | Hess et al. | |
| 2008/0078801 A1 | 4/2008 | Shelton, IV et al. | |
| 2008/0078802 A1 | 4/2008 | Hess et al. | |
| 2008/0078803 A1 | 4/2008 | Shelton, IV et al. | |
| 2008/0078804 A1 | 4/2008 | Shelton, IV et al. | |
| 2008/0078805 A1 | 4/2008 | Omaits et al. | |
| 2008/0078806 A1 | 4/2008 | Omaits et al. | |
| 2008/0078807 A1 | 4/2008 | Hess et al. | |
| 2008/0081881 A1 | 4/2008 | Swetlin et al. | |
| 2008/0082124 A1 | 4/2008 | Hess et al. | |
| 2008/0082126 A1 | 4/2008 | Murray et al. | |
| 2008/0110959 A1 | 5/2008 | Orban, III et al. | |
| 2008/0114381 A1 | 5/2008 | Voegele et al. | |

(56) References Cited

U.S. PATENT DOCUMENTS

| | | | |
|---|---|---|---|
| 2008/0114385 A1 | 5/2008 | Byrum et al. | |
| 2008/0114399 A1 | 5/2008 | Bonutti | |
| 2008/0125812 A1 | 5/2008 | Zubik et al. | |
| 2008/0128469 A1 | 6/2008 | Dalessandro et al. | |
| 2008/0140115 A1 | 6/2008 | Stopek | |
| 2008/0200949 A1 | 8/2008 | Hiles et al. | |
| 2008/0314960 A1 | 12/2008 | Marczyk et al. | |
| 2009/0001122 A1 | 1/2009 | Prommersberger et al. | |
| 2009/0076510 A1 | 3/2009 | Bell et al. | |
| 2009/0118747 A1 | 5/2009 | Bettuchi et al. | |
| 2009/0134200 A1* | 5/2009 | Tarinelli et al. | 227/180.1 |
| 2009/0206125 A1 | 8/2009 | Huitema et al. | |

FOREIGN PATENT DOCUMENTS

| | | |
|---|---|---|
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 98/38923 | 9/1998 |
| WO | WO 99/45849 | 9/1999 |
| WO | WO 01/17446 | 3/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |
| WO | WO 2010/028332 | 3/2010 |

OTHER PUBLICATIONS

Abstract for FR2789885, Aug. 25, 2000.
Abstract for FR2850281, Jul. 30, 2004.
Abstract for JP1072740, Mar. 17, 1989.
Abstract for JP11309151, Nov. 9, 1999.
Abstract for JP3146773, Jun. 21, 1991.
Abstract for JP5076586, Mar. 30, 1993.
International Preliminary Report on Patentability dated Mar. 18, 2014 for Application No. PCT/US2012/054388.

* cited by examiner

SURGICAL STAPLE CARTRIDGE WITH SELF-DISPENSING STAPLE BUTTRESS

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in; U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,964,363, entitled "Surgical Stapling Instrument having Articulation Joint Support Plates for Supporting a Firing Bar," issued Nov. 15, 2005; U.S. Pat. No. 6,978,921, entitled "Surgical Stapling Instrument Incorporating an E-Beam Firing Mechanism," issued Dec. 27, 2005; U.S. Pat. No. 6,988,649, entitled "Surgical Stapling Instrument Having a Spent Cartridge Lockout," issued Jan. 24, 2006; U.S. Pat. No. 7,000,818, entitled "Surgical Stapling Instrument Having Separate Distinct Closing and Firing Systems," issued Feb. 21, 2006; U.S. Pat. No. 7,111,769, entitled "Surgical Instrument Incorporating an Articulation Mechanism having Rotation about the Longitudinal Axis," issued Sep. 26, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument having Multistroke Firing with Opening Lockout," issued Oct. 14, 2008; U.S. Pat. No. 7,721,930, entitled "Disposable Cartridge with Adhesive for Use with a Stapling Device," issued May 25, 2010; and U.S. Pat. No. 7,455,208, entitled "Surgical Instrument with Articulating Shaft with Rigid Firing Bar Supports," issued Nov. 25, 2008. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
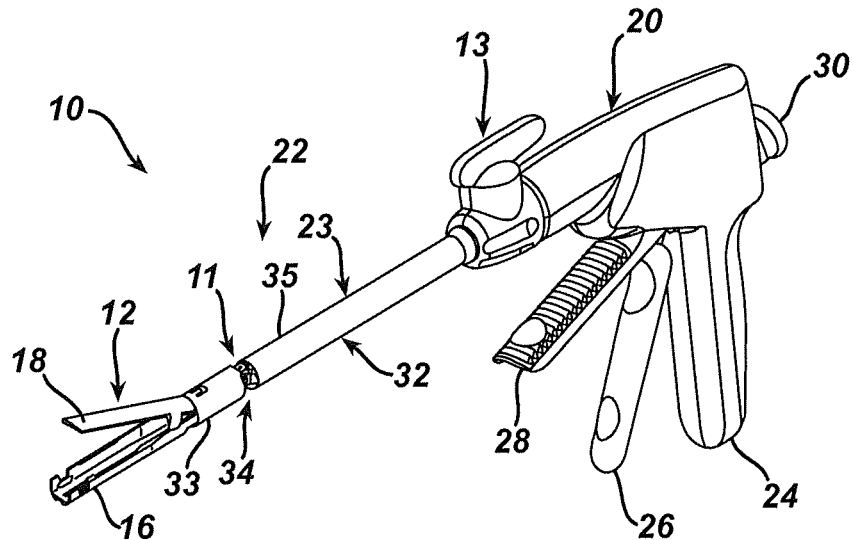
FIG. 1A depicts a perspective view of an articulating surgical instrument with an end effector in a nonarticulated position.
Figure 1B:
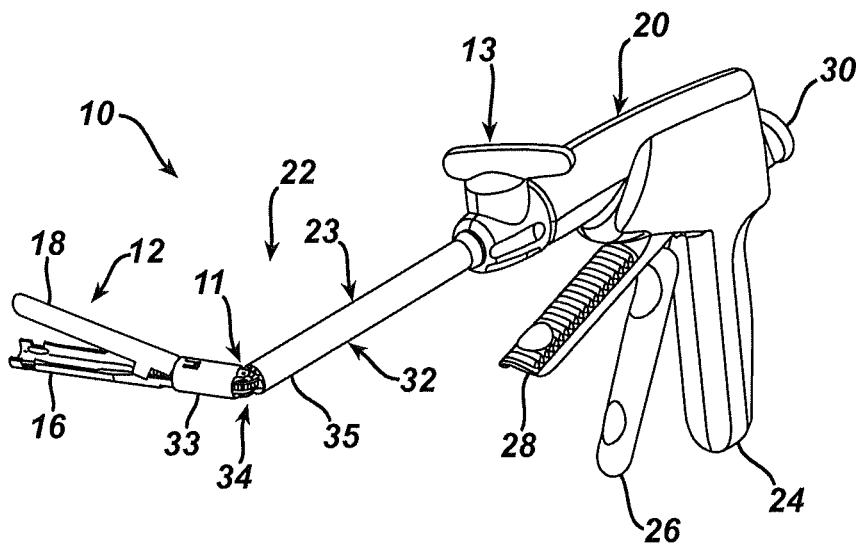
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical and stapling and severing instrument (10) includes handle portion (20) connected to implement portion (22), the latter further comprising shaft (23) distally terminating in an articulating mechanism (11) and a distally attached end effector (12). Once articulation mechanism (11) and distally end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal portion (closure ring) (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
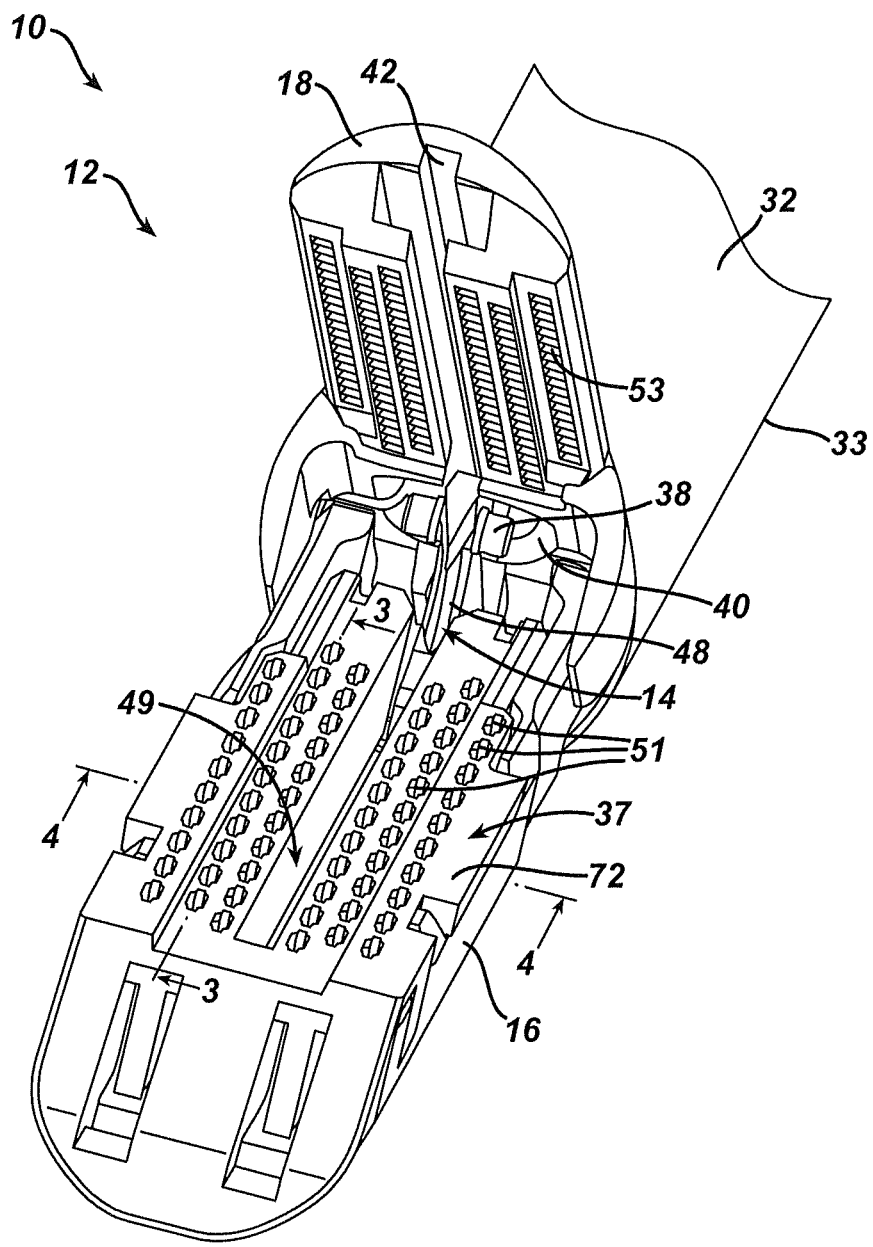
FIG. 2 depicts a perspective view of an opened end effector of the surgical instrument of FIGS. 1A-1B.
Figure 3A:
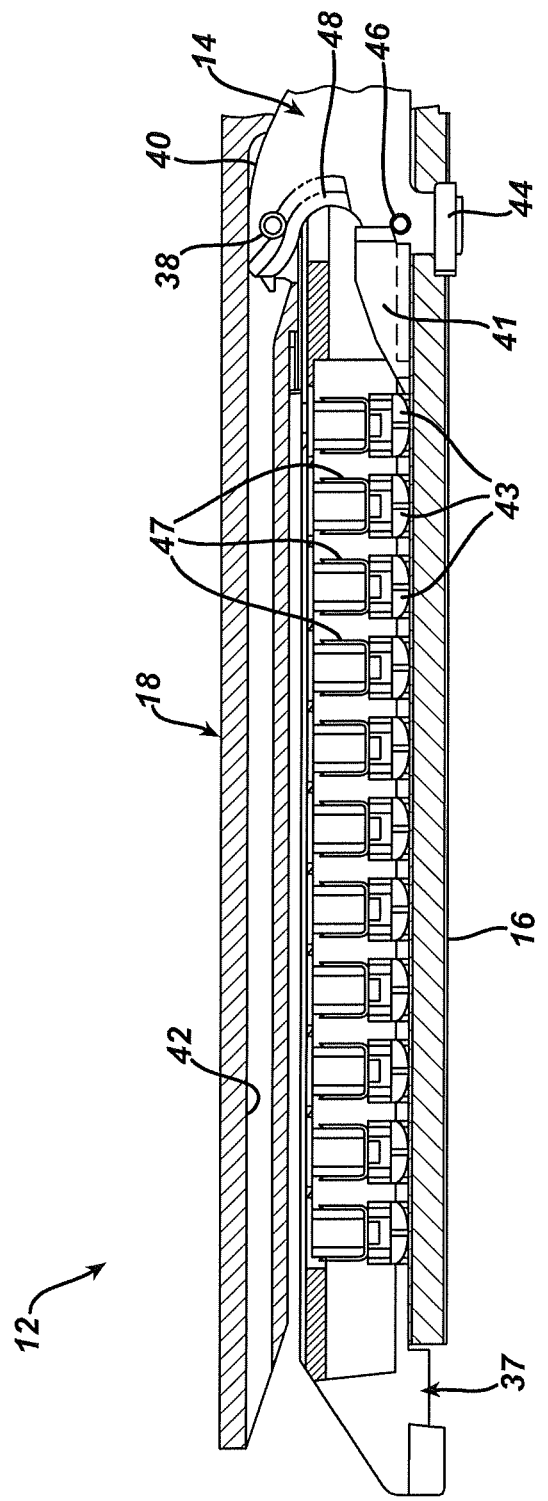
FIG. 3A depicts a side cross-sectional view of the end effector of FIG. 2, taken along line 3-3 of FIG. 2, with the firing bar in a proximal position.
Figure 3B:
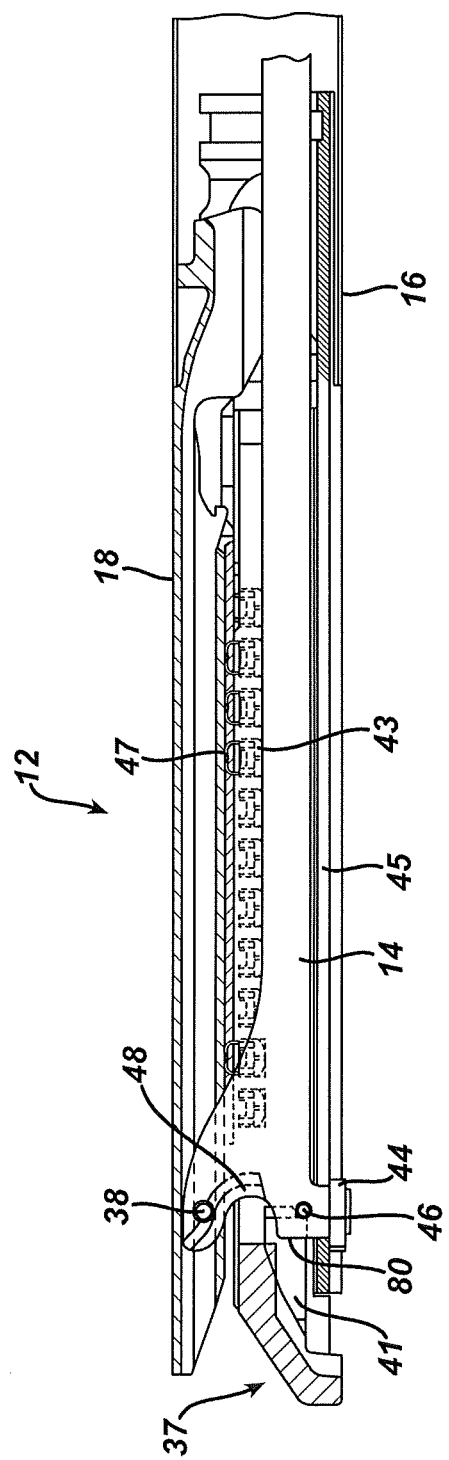
FIG. 3B depicts a side cross-sectional view of the end effector of FIG. 2, taken along line 3-3 of FIG. 2, but showing the firing bar in a distal position.
Figure 4:
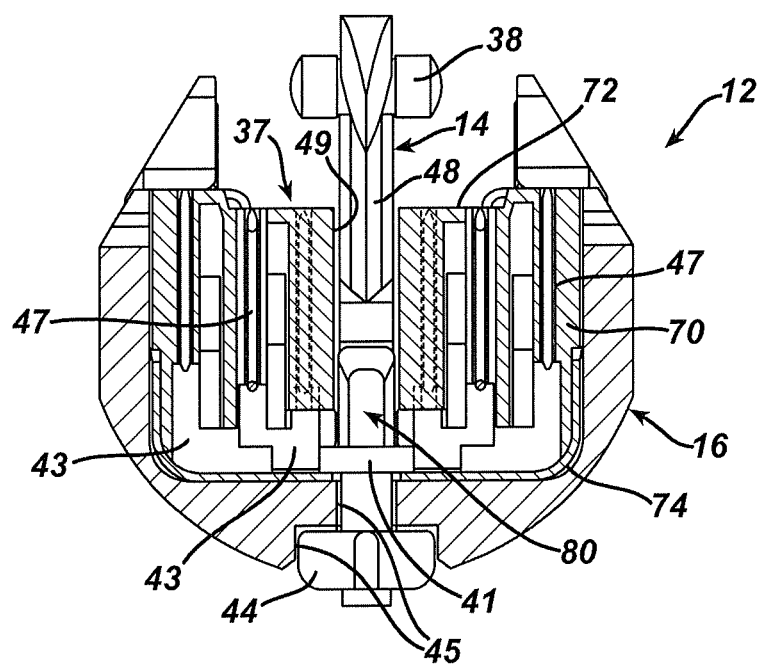
FIG. 4 depicts an end cross-sectional view of the end effector of FIG. 2, taken along line 4-4 of FIG. 2.
Figure 5:
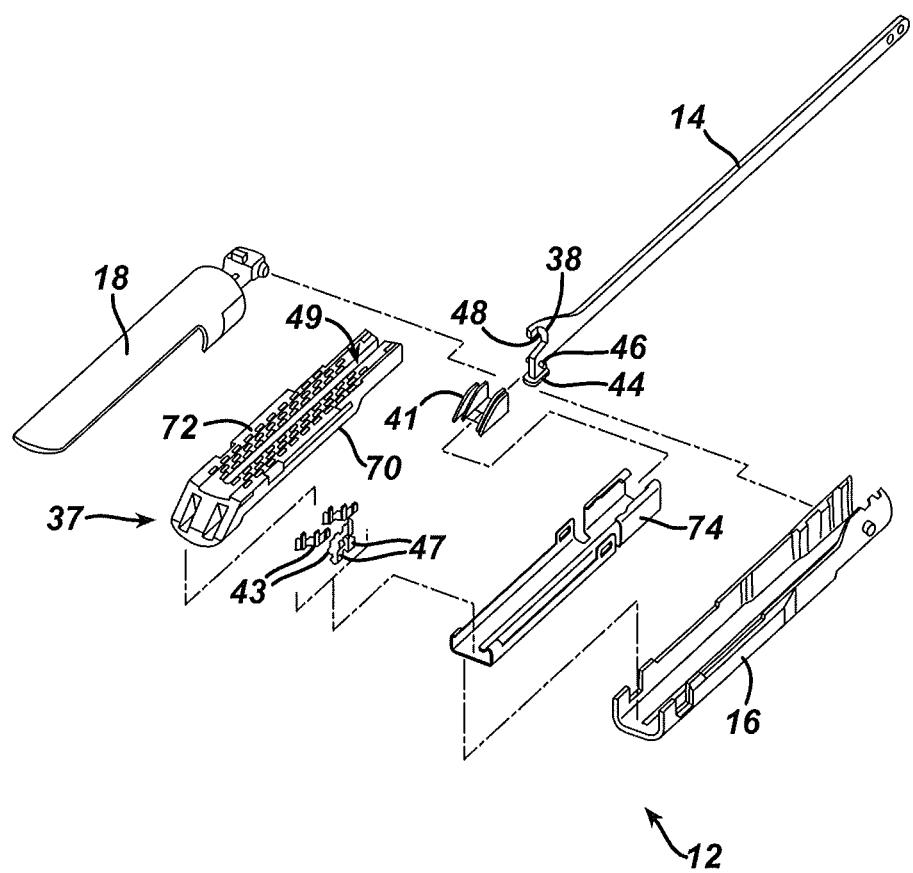
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (70) on one side of vertical slot (49), with another set of three rows of staple apertures (51) being formed through upper deck (70) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into a firing slot within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
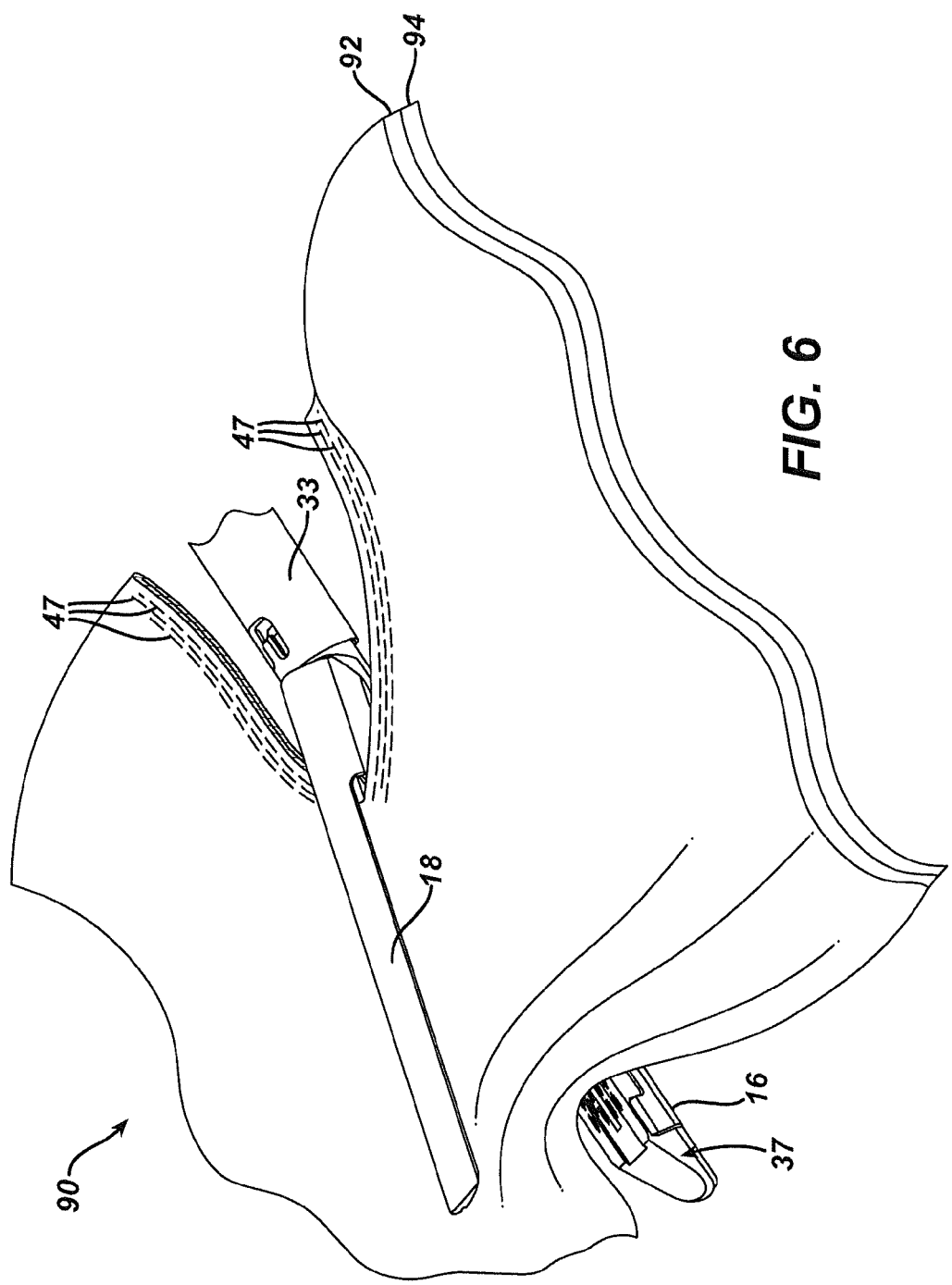
FIG. 6 depicts a perspective view of the end effector of FIG. 2, positioned at tissue and having been actuated once in the tissue.

FIG. 6 shows end effector (12) having been actuated through a single stroke through tissue (90). As shown, cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,964,363; U.S. Pat. No. 6,978,921; U.S. Pat. No. 6,988,649; U.S. Pat. No. 7,000,818; U.S. Pat. No. 7,111,769; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; and/or U.S. Pat. No. 7,455,208. As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Self-Dispensing Buttress Integral with a Cartridge

Figure 7A:
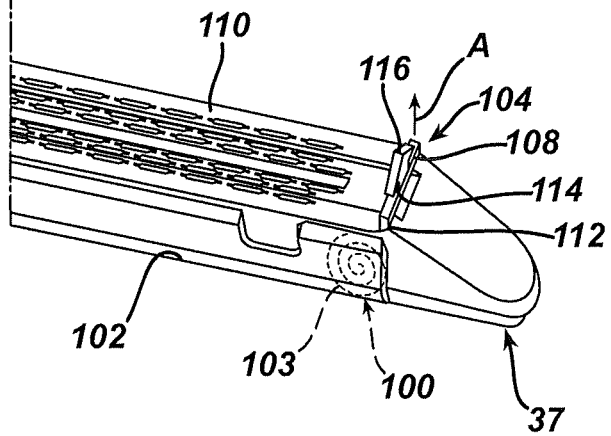
FIG. 7A depicts a perspective, fragmentary view of a cartridge of the end effector of FIG. 2 including an exemplary integral self-dispensing buttress, the buttress in a first, retracted position in which it is unattached to the anvil.
Figure 7B:
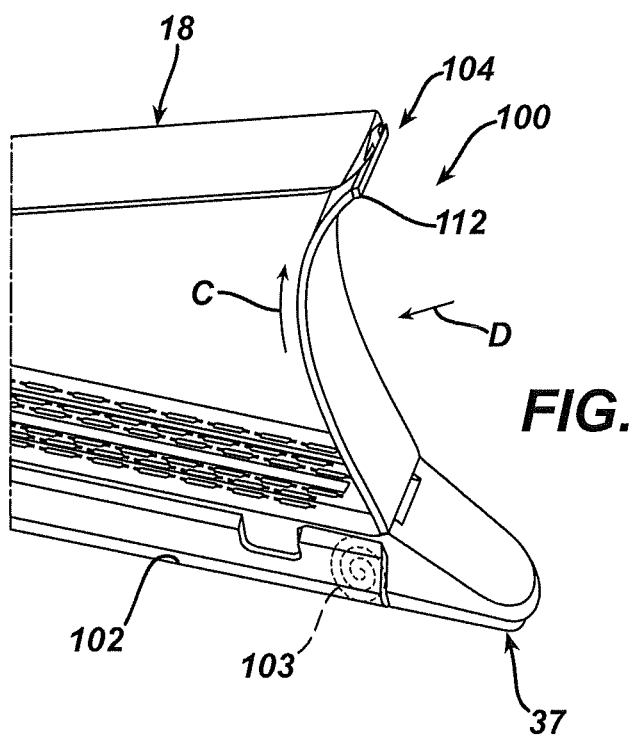
FIG. 7B depicts a perspective, fragmentary view of the buttress of FIG. 7A in a second, extended position in which it is attached to the anvil.

FIGS. 7A-7B show an exemplary self-dispensing buttress (100) integral to cartridge (37). FIG. 7A shows buttress (100) in a first, retracted position in which buttress (100) is not yet attached to anvil (18) and a retained portion of buttress (100) is housed in cartridge (37). FIG. 7B shows buttress (100) in a second, extended position in which buttress (100) has been attached to anvil (18) and an exposed portion of buttress (100) is available for receipt of tissue (90), as described below.

As shown in FIG. 7A, buttress (100) may be disposed within the body of cartridge (37) above cartridge pan (102) in a rolled formation such as buttress roll (103). Roll (103) is disposed near a distal end of cartridge (37). Buttress (100) includes a fastener, such as T-shaped fastener (104), which is attachable to opening (106) defined in a corresponding distal end of anvil (18). Opening (106) is sized for receipt of fastener (104). Fastener (104) includes elongate portion (108) that is disposed adjacent exterior top surface (110) of cartridge (37) in the retracted position shown in FIG. 7A. End (112) of buttress (100) is attached to elongate portion (108). End (112) extends through an aperture (not shown) defined in cartridge (37), the aperture having a shape that corresponds to and is slightly larger than end (112). Such a shape of the aperture allows buttress (100) to be removed from cartridge (37) as described below. While elongate portion (108) is shown to have a width substantially similar to the width of exterior top surface (110), the width of elongate portion (108) may alternatively be greater or less than the width of exterior top surface (110) of cartridge (37).

Intermediate portion (114) projects from elongated portion (108) in the direction of arrow (A) toward anvil (18). Triangular portion (116) projects from intermediate portion (114) in the direction of arrow (A). Walls of the corresponding distal end of anvil (18), and particularly at a distal end of anvil slot (42) as shown in FIG. 3A, define opening (106). Opening (106) includes first portion (118) sized for receipt of intermediate portion (114) and second portion (120) sized for receipt of triangular portion (116). Portions (114, 116) of fastener (104) may be received in respective portions (118, 120) in, for example, a snap-fit connection. Portions (114, 116) may be positioned adjacent respective portions (118, 120) and pressed into place in a snap-fit connection to attach fastener (104) to anvil (18) via opening (106). Fastener (104) may comprise a variety of shapes, and opening (106) may comprise a variety of corresponding shapes sized to receive fastener (104), such that fastener (104) and opening (106) are operable to removably secure fastener (104) to anvil (18). To attach fastener (104) to anvil (18), fastener (104) may be urged upwards towards anvil (18) in the direction of arrow (A) and secured within opening (106). Alternatively or additionally, anvil (18) may be directed downwards in the direction of arrow (B) towards cartridge (37) to a position at which fastener (104) may be secured within opening (106). For example, closure trigger (26) may be actuated before insertion of end effector (12) into a trocar, in a manner as described above, such that closure sleeve (32) longitudinally translates with respect to handle portion (20) to close anvil (18) toward lower jaw (16) of end effector (12). After attachment to buttress (100), anvil (18) will be directed in the direction of arrow (A) towards an initial, open position, as shown in FIG. 7B. As anvil (18) is directed towards the initial, open position, buttress (100) will unwrap from roll (103) and be moved or urged upwards in the direction of arrow (C). In particular, end (112) of buttress (100) is attached to fastener (104), which provides a force upon buttress (100) when fastener (104) is directed upwards in the direction of arrow (B).

Continuing to refer to FIG. 7B, when buttress (100) is attached to anvil (18) via fastener (104), buttress (100) may receive a material, such as tissue (90). Tissue (90) may urge buttress (100) proximally inwards, in the direction of arrow (D), toward an interior space defined between cartridge (37) and anvil (18) of end effector (12). As buttress (100) is urged in the direction of arrow (D), buttress (100) will unwrap from roll (103) so that a sufficient amount of buttress (100) is exposed from the retained portion of buttress (100). The exposed portion may retain tissue (90) that urges it proximally inwards into the interior space. Additionally, roll (103) could be resiliently biased to retract, to reduce inadvertent unwrapping of buttress (100).

Figure 10:
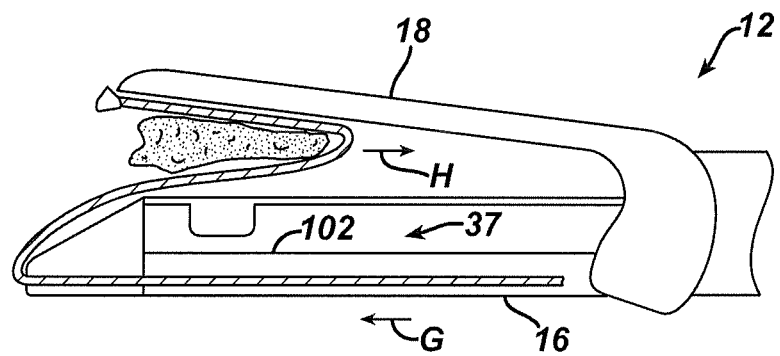
FIG. 10 depicts a elevation view of the end effector of FIG. 2 including the buttress of FIG. 9 in which tissue is received within an intermediate portion of the buttress to push the buttress proximally into a space between the cartridge and the anvil of the end effector.

In use, after fastener (104) is attached to anvil (18) and tissue (90) has urged buttress (100) inwards, end effector (12) will operate as described above to sever and staple tissue (90) while additionally driving staples (47) through buttress (100) and slicing through portions of buttress (100). The effect will be to dispose portions of buttress (100) onto tissue (90). Buttress (100) may be composed of a material including, for example, a hemostatic agent to assist to coagulate blood and reduce bleeding at the severed and/or stapled surgical site along tissue (90). In addition or in the alternative, buttress (100) may comprise a biodegradable polymer operable to assist with tissue repair as described below. Material of buttress (100) severed by firing bar (14) may be deposited onto tissue (90). Additionally, when surgical staple (47) is driven into tissue by a surgical instrument, such as by instrument (10) in the manner disclosed above, surgical staple (47) will compress, connect, and retain such tissue as shown in FIG. 10. Material from buttress (100) will contact the compressed tissue and release onto the tissue to assist with tissue repair by reducing the amount of bleeding at the surgical site. In addition or in the alternative, buttress (100) may provide reinforcement to the integrity of the mechanical attachment of tissue (90) by staples (47). Surgical staple (47) may comprise a material selected from iron, nickel titanium alloy, stainless steel, and/or titanium. Of course, any other suitable materials may be used.

The material for buttress (100) may comprise, for example, adjunct or hemostatic agents such as fibrin or thrombin that assist to coagulate blood and reduce the amount of bleeding at the surgical site. The hemostatic abilities of such adjuncts may also contribute to the use of such adjuncts as adhesives and sealants. The agents may assist to coagulate blood at a surgical site which allows tissue surrounding such blood to stick together and may prevent leaks along the stapled tissue site, for example.

Such adjuncts or reagents may further include but are not limited to medical fluid or buttress components. Preferred materials are natural or genetically engineered absorbable polymers or synthetic absorbable polymers, or mixtures thereof. Examples of natural or genetically engineered absorbable polymers are proteins, polysaccharides and combinations thereof. Proteins include, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopres sin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of synthetic absorbable polymers are aliphatic polyester polymers, copolymers, and/or combinations thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one). Other suitable compounds, materials, substances, etc., that may be used in a medical fluid or buttress will be apparent to those of ordinary skill in the art in view of the teachings herein.

In some versions, a medical fluid may be suspended in a biocompatible carrier to form the material of buttress (100). Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include proteins, polysaccharides, polynucleotides, and other materials such as alginate, cross-linked alginate, poly (N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers, and combinations of any of the foregoing.

Buttress (100) may comprise a fibrous pad, a foam, a matrix, a mesh, or another structure, in accordance with the teachings of, by way of example, U.S. Patent App. Pub. No. 2009/0120994, entitled "Surgical Fastening Device with Initiator Impregnation of a Matrix or Buttress to Improve Adhesive Application", published May 14, 2009, issued as U.S. Pat. No. 7,708,180 on May 4, 2010, the disclosure of which is incorporated by reference herein. The material may comprise, for example, a biocompatible material that is a buttress, a matrix having a plurality of openings therein, an open cell foam, a closed cell foam, and/or a fabric pad. The material may include porosities that induce a wicking feature to drawing adhesive into the material and ensure the openings remain clear of the adhesive, allowing tissue growth through the openings after application to tissue. Other suitable materials and compositions that may be used to form buttress (100) will be apparent to those of ordinary skill in the art in view of the teachings herein.

III. Another Exemplary Self-Dispensing Buttress Integral with a Cartridge

Figure 8:
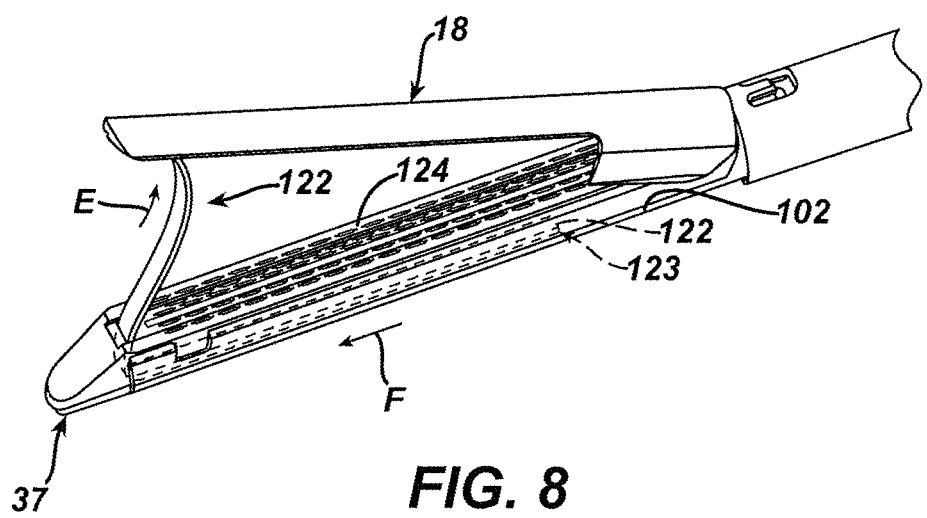
FIG. 8 depicts a perspective, fragmentary view of a cartridge of the end effector of FIG. 2 including another exemplary integral self-dispensing buttress, the buttress in an open position in which it is attached to the anvil.

FIG. 8 shows another exemplary self-dispensing buttress (122) integral to cartridge (37). FIG. 8 shows buttress (122) in a position in which buttress (100) has been attached to anvil (18). Buttress (122) may be attached to anvil (18) in a similar manner as that described above to attach buttress (100) to anvil (18).

Buttress (122) is disposed within the body of cartridge (37), between top surface (124) of cartridge (37) and bottom cartridge pan (102) of cartridge (37). Rather than being stored in a roll within cartridge (37), buttress (122) is stored in a substantially flat manner and substantially parallel to cartridge pan (102). Buttress (122) may be disposed below staples (47), drivers (43), and wedge sled (41) that are contained without the housing of cartridge (37). Buttress (122) may have a width that corresponds to or is slightly less than the width of cartridge pan (102). Alternatively, cartridge pan (102) may be modified to include internal walls configured to hold a length of buttress (122), and buttress (122) may then have a width that corresponds to or is slightly less than the width of the internal walls. Buttress (122) may also be disposed below cartridge pan (102). Cartridge pan (102) may include, for example, external walls configured to hold a length of buttress (122) to retain buttress (122) while allowing portions of buttress (122) to travel longitudinally, for example, in the direction of arrow (E) of FIG. 8. It should be understood that, in the present example, free end (123) of buttress (122) may travel freely within or below cartridge pan (102).

A portion of buttress (122) is received and urged through aperture (128) defined within top surface (124) at a distal end of cartridge (37). In particular, after attachment to buttress (122), anvil (18) will be directed in the direction of arrow (E) towards an open position, as shown in FIG. 8. As anvil (18) is directed towards the initial, open position, buttress (122) will be linearly and distally pulled in the direction of arrow (F) and be pulled upwards in the direction of arrow (E). In particular, an end of buttress (120) is attached to a fastener, such as end (112) of buttress (100) attaches to fastener (104), described above. Similarly, a force is provided upon buttress (122) when the attached fastener is directed upwards in the direction of arrow (E).

As described above with respect to buttress (100), buttress (122) may receive a material, such as tissue (90). Buttress (122) may operate in a similar manner as buttress (100) to extend about tissue (90) and to have exposed portions of buttress (122) driven with staples (47) and/or firing bar (14) onto portions of tissue (90).

IV. An Exemplary Self-Dispensing Buttress Integral with a Lower Jaw

Figure 9:
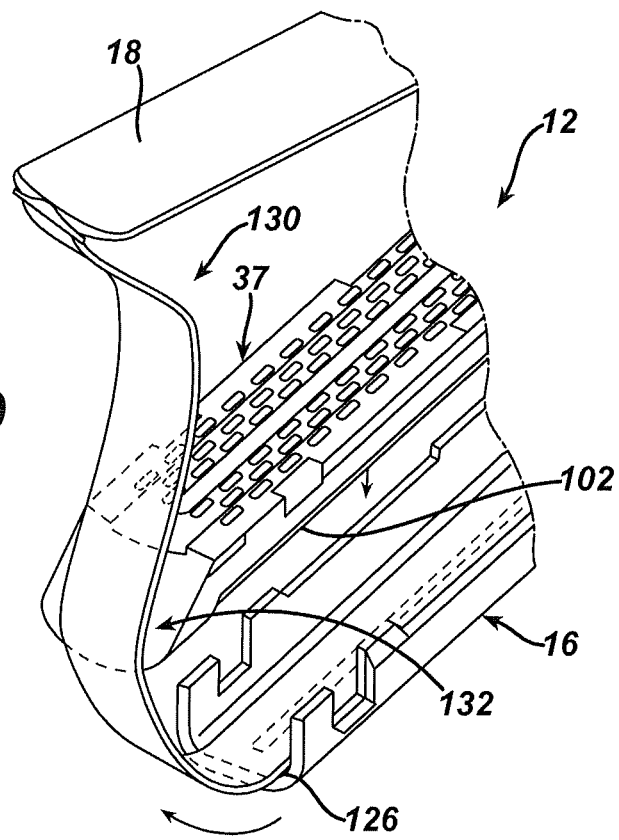
FIG. 9 depicts a perspective, fragmentary exploded view of a lower jaw of the end effector of FIG. 2 including another exemplary integral self-dispensing buttress, the buttress in an open position in which it is attached to the anvil.

FIG. 9 shows another exemplary self-dispensing buttress (130) in a position in which buttress (130) has been attached to anvil (18). Buttress (130) may be attached to anvil (18) in a similar manner as that described above to attach buttresses (100, 122) to anvil (18). Buttress (130) is disposed between cartridge pan (102) and lower jaw (16) of end effector (12). Lower jaw (16), as described above, is configured to receive cartridge (37). Lower jaw (16) may be configured to accommodate a removable and replaceable length of buttress (130).

Rather than being stored in a roll within cartridge (37), buttress (122) is stored in a substantially flat manner along surface (126) of lower jaw (16) disposed opposite cartridge pan (102) when cartridge (37) is received within lower jaw (16). Buttress (122) may have a width that corresponds to or is slightly less than the width of lower jaw (16). Alternatively, lower jaw may be modified to include internal walls configured to hold a length of buttress (130), such that buttress (130) may have a width that corresponds to or is slightly less than the width of the internal walls.

When cartridge (37) is received within lower jaw (16) and on top of buttress (130), a sufficient space exists such that buttress (130) may be pulled linearly and distally the direction of arrow (G) and be urged around distal end (132) of cartridge (37). Tissue (90) wrapped by buttress (130) moves proximally inwards in the direction of arrow (H) in a manner similar to that described above for buttresses (100, 122), as opened end effector (12) is advanced over tissue (90) to "bite" tissue (90).

As described above with respect to buttress (100), and as shown in FIG. 10, buttress (130) may receive a material, such as tissue (90). Buttress (130) may operate in a similar manner as buttress (100) to extend about tissue (90) and to have exposed portions of buttress (122) driven with staples (47) and/or firing bar (14) onto portions of tissue (90).

Figure 11:
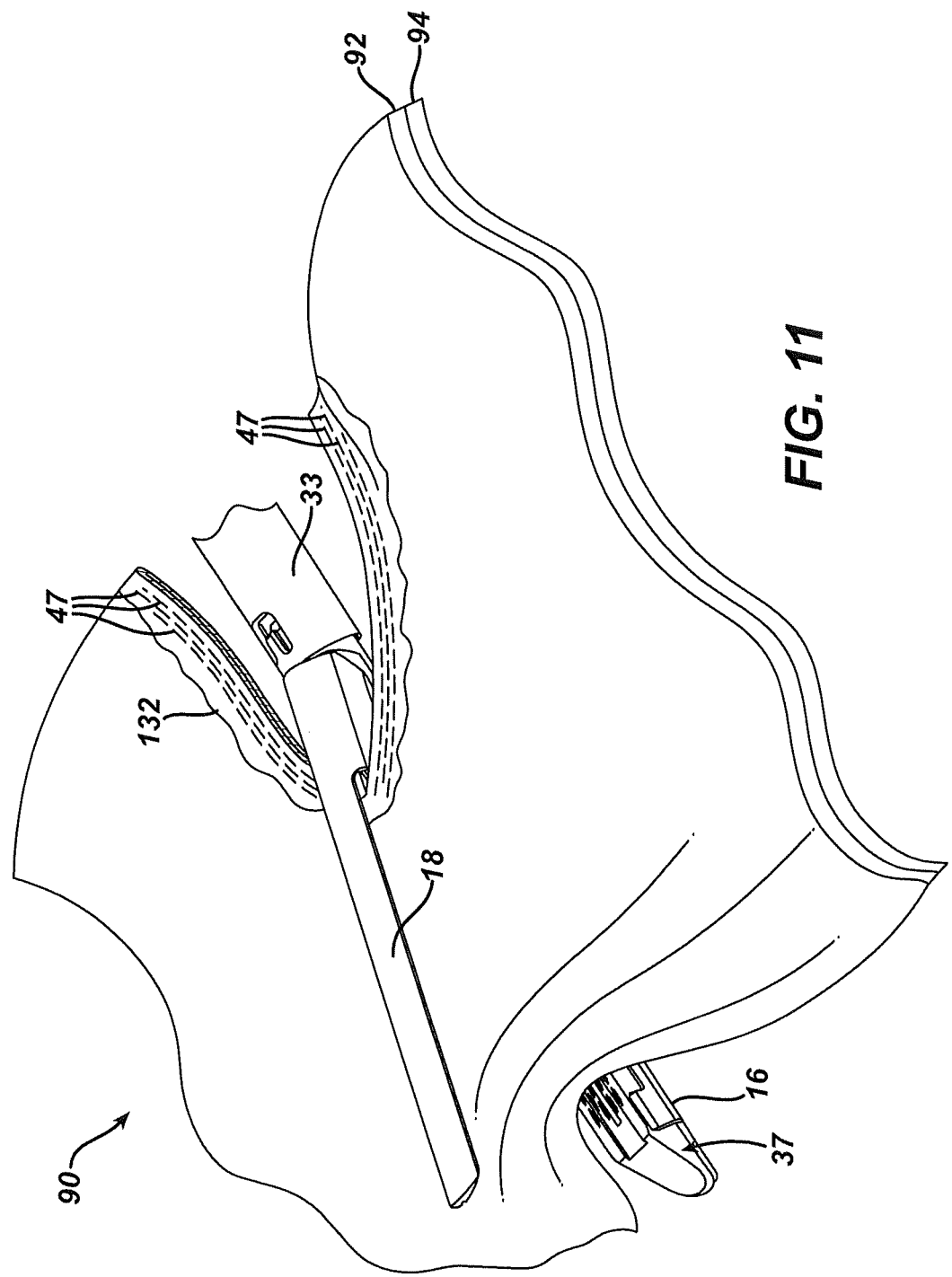
FIG. 11 depicts a perspective view of an end effector with an integral self-dispensing buttress, the end effector positioned at and actuated within the tissue to release a tissue repair composition from the buttress onto the tissue.

FIG. 11 shows an example of using end effector (12) to apply one of the exemplary buttresses (100, 122, 130) described herein onto tissue (90) to deposit tissue repair composition (132) onto tissue (90). After such an application as described above, tissue repair composition (132) of and released by the respective buttress (100, 122, 130) substantially surrounds and is coated onto staples (47) that compress layers of tissue (90).

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) a shaft housing a firing bar;
   (c) an end effector comprising an anvil, a lower jaw, and a stapling and severing assembly responsive to a longitudinal closing motion produced by the body and the shaft;
   (d) a removable cartridge, wherein the lower jaw is configured to receive a cartridge when the end effector is in an open configuration, the cartridge comprising:
      (i) a housing,
      (ii) a plurality of staples disposed in the housing, and
      (iii) a deck disposed over the plurality of staples, the deck defining apertures, each aperture being substantially disposed over each staple; and
   (e) a movable buttress that is integral with the housing of the cartridge or integral with the lower jaw of the end effector, wherein the buttress is disposed in a roll within the housing of the cartridge, the buttress being movable relative to the cartridge and relative to the end effector.

2. The surgical instrument of claim 1, wherein the roll is resiliently biased.

3. The surgical instrument of claim 1, wherein the buttress is disposed in a substantially flat position within the housing of the cartridge.

4. The surgical instrument of claim 3, wherein a free end of the buttress is configured to travel freely within the housing of the cartridge.

5. The surgical instrument of claim 1, wherein the housing of the cartridge comprises a cartridge pan, wherein the cartridge pan is configured to receive the buttress in a substantially flat position.

6. The surgical instrument of claim 1, the housing of the cartridge comprises a cartridge pan, wherein the buttress is disposed in a substantially flat position on an exterior, underside surface of the cartridge pan.

7. The surgical instrument of claim 1, wherein the housing of the cartridge comprises a cartridge pan, wherein an underside of the cartridge pan includes exterior walls, wherein the exterior walls are configured to receive the buttress in a substantially flat position.

8. The surgical instrument of claim 1, wherein the buttress is disposed in a substantially flat position along an interior surface of the lower jaw of the end effector, wherein the interior surface is configured to receive the removable cartridge.

9. The surgical instrument of claim 1, wherein the lower jaw of the end effector comprises interior walls, wherein the interior walls are configured to receive the removable cartridge, wherein the interior walls are further configured to receive the buttress in a substantially flat position.

10. The surgical instrument of claim 1, wherein an end of the buttress comprises a fastener.

11. The surgical instrument of claim 10, wherein a distal end of the anvil defines an opening configured to receive the fastener of the buttress.

12. The surgical instrument of claim 1, wherein the buttress comprises a biocompatible material selected from a group consisting of at least one of the following materials: epsilon-caprolactone glycolide, bovine pericardium, polylactic acid, polyglycolic acid, polyglactin, polydioxanone, polyglyconate, whey protein, cellulose gum, starch, gelatin, silk, nylon, polypropylene, braided polyester, polybutester, polyethylene, and polyetheretherketones.

13. The surgical instrument of claim 1, wherein the buttress comprises one of fibrin or thrombin.

14. The surgical instrument of claim 1, wherein the buttress is configured to provide reinforcement to the mechanical integrity of the staples when the staples are driven through the buttress and towards the anvil.

15. A surgical instrument, comprising:
   (a) a body;
   (b) a shaft housing a firing bar;
   (c) an end effector comprising an anvil, a lower jaw, and a stapling and severing assembly responsive to a longitudinal closing motion produced by the body and the shaft;
   (d) a removable cartridge, wherein the lower jaw is configured to receive a cartridge when the end effector is in an open configuration, the cartridge comprising:
      (i) a housing,
      (ii) a plurality of staples disposed in the housing, and
      (iii) a deck disposed over the plurality of staples, the deck defining apertures, each aperture being substantially disposed over each staple; and
   (e) a movable buttress that is integral with the housing of the cartridge or integral with the lower jaw of the end effector, the buttress being movable relative to the cartridge and relative to the end effector, wherein an end of the buttress comprises a fastener, wherein a distal end of the anvil defines an opening configured to receive the fastener of the buttress.

* * * * *